United States Patent [19]
Bodman

[11] Patent Number: 5,265,625
[45] Date of Patent: Nov. 30, 1993

[54] HEAD IMMOBILIZER

[76] Inventor: Moshe Bodman, 464 Hidden Trail, Willowdale, Ontario, M2R 3R8, Canada

[21] Appl. No.: 984,775

[22] Filed: Dec. 3, 1992

[51] Int. Cl.⁵ .................. A61B 19/00; A61F 5/37; A47C 20/02
[52] U.S. Cl. .................. 128/869; 128/870; 128/875; 5/637
[58] Field of Search .............. 5/628, 622, 633, 637; 128/869–876; 602/19

[56] References Cited

U.S. PATENT DOCUMENTS

| | | | |
|---|---|---|---|
| 933,471 | 9/1909 | Leahy | 5/637 |
| 3,343,180 | 9/1967 | Lothschuetz | 5/628 |
| 3,814,942 | 6/1974 | Darden | 5/637 |
| 3,889,668 | 6/1975 | Ochs | 128/870 |
| 3,897,777 | 8/1975 | Morrison . | |
| 4,034,748 | 7/1977 | Winner . | |
| 4,182,322 | 1/1980 | Miller . | |
| 4,211,218 | 7/1980 | Kendrick . | |
| 4,275,472 | 6/1981 | Erck | 5/622 |
| 4,285,081 | 8/1981 | Price | 5/637 |
| 4,297,994 | 11/1981 | Beshaw . | |
| 4,528,981 | 7/1985 | Behar . | |
| 4,589,407 | 5/1986 | Koledin . | |
| 4,640,275 | 2/1987 | Buzzese . | |
| 4,854,305 | 8/1989 | Bremer | 128/870 |
| 4,905,712 | 3/1990 | Bowlin | 5/637 |
| 4,911,179 | 3/1990 | Brown | 128/875 |
| 4,928,711 | 5/1990 | Williams . | |

Primary Examiner—Michael A. Brown
Attorney, Agent, or Firm—Bereskin & Parr

[57] ABSTRACT

A device for immobilizing the head to prevent further injuries such as neck injuries comprises left and right complimentary blocks. Each block has a skull supporting surface. The blocks contact the skull with the skull supporting surfaces diverging outwardly and upwardly to provide a wedging action to immobilize the skull against left and right movement as well as to position the height of the skull so that alignment of the neck is achieved. The skull supporting surface surrounds but does not cover the ear so that assessment may be made easily. The left and right blocks may be disposable for one time use or permanently mounted on a carrier for reuse.

19 Claims, 4 Drawing Sheets

HEAD IMMOBILIZER

FIELD OF THE INVENTION

The present invention is related to head or cervical immobilization devices and more particularly to an improved immobilizer for constraining the head and upper cervical portions of a person against movement during transport on a rigid patient support back board and during transport within a medical facility and during medical evaluation including techniques such as x-rays, CT scans and the like.

BACKGROUND ART

It has long been recognized that it is of vital importance to stabilize the head and cervical portions of accident victims or those who are suspected of having been exposed to cervical injuries. It is well understood that very serious and permanent damage can be done by movement of the head and cervical portions when damage has occurred in the cervical region. Accordingly, with accident victims or others in whom possibility of head or cervical injury exists, the paramedical staff attending the patient at the site and during transference to a medical treatment facility routinely immobilize the head and cervical spinal area of such a patient to attempt to reduce any further injury. Similarly upon arrival of accident victims or the like at a medical treatment facility, medical staff then must assess the patient while ensuring that no additional damage is done during the assessment process. Often the assessment process may involve use of other sophisticated medical equipment located in other areas of the hospital or treatment facility other than the emergency or receiving room. This may involve moving the patient to be subjected to x-ray evaluation or CT scans and the like. During the medical evaluation procedure it is important and desirable that full access be had to the head and cervical area of the patient without moving the patient.

There have been many devices intended to maintain support for the head of a patient during the transport phase from accident scene to medical treatment facility. U.S. Pat. No. 4,182,322 issued Jan. 8, 1980 to Miller discloses a durable lightweight three section cushion which is used to effectively cover and restrain the head of the accident victim when placed on a body splint or a back board. The cushion presents a substantially box-like structure extending over the top of the patient's head and along either side. Straps are positioned across the forehead and jaw of the patient.

U S. Pat. No. 4,297,994 issued Nov. 3, 1981 to Beeshaw illustrates a similar device in which a pair of relatively large rectangular blocks are positioned on either side of the patient's head extending from adjacent the shoulder to above the top of the head. A strap extending across the top of the head connects the two blocks. Immobilization straps may then be placed running across the patient's forehead and jaw extending from the outside surfaces of the square blocks.

U.S. Pat. No. 4,528,981 issued Jul. 16, 1985, to Behar illustrates a cervical immobilization device comprising a pair of cylindrical support rolls one extending on either side of the head, the axis of the roll extending substantially parallel to the spine. Straps extending from each roll cross over the patient's forehead and jaw to maintain the location of the head and to stabilize against movement.

There have also been a number of proposals for use of relatively cheap, reasonably disposable supports made from a single piece of material such as corrugated material, sheet plastic, cardboard or other material which is light in weight and which can be folded for storage and use. One example of this type of device is illustrated in U.S. Pat. No. 4,928,711 issued May 29, 1990 to Williams. The Williams device includes a pair of laterally extending side support panels. Each of the side panels includes an inner panel and an outer panel with the inner panel being conformable to a shape necessary to support the head of the patient. The inner panel also includes an opening which divides a portion of that inner panel into a pair of spaced support members which extend laterally from the base. The outer panel has inner and outer edges and is attached by a hinge to the inner panel such that it is foldable relative to the inner panel to provide a substantially rigid brace for securing the inner panel in the desired immobilizing position. The outer panel also includes a cut out portion for providing substantial access to the opening of the inner panel when in the braced configuration.

While many of the prior devices are effective to stabilize the head and cervical region of the spine against movement during transport the head supporting structure does not allow for assessment by medical staff. Typically, when there is injury in the region of the head or in the region of the neck it is desirable to have access to the ear so as to be able to view bleeding from the ear or discharge from the ear and the like which may be useful in assessing medical conditions. With prior art structures that involve rolls, blocks or panels that extend along the side of the head it becomes impossible to assess for head injuries and the like without removing the supporting structure. Thus, before any detailed assessment can be carried out the head immobilizing structure must be removed and some different structure installed in its place during that initial assessment. It is also desirable in many instances to be able to use the standard forms of cervical collar to provide support for the patient's cervical region while also immobilizing the head. It is often desirable to provide the cervical collar rather than simply immobilizing the head. Thus it is desirable that a head immobilizing structure permit the use of a cervical collar.

One of the major areas which devices as referred to above and many others of this type do not address is the question of the elevation of the head. Different body configurations will result in different alignments of the spine when the patient is placed on a hard supporting surface such as a back board or stretcher. Depending upon the configuration of the patient's back, the head may in fact tip backward thus bending the cervical spine backward before the head contacts the surface of the backboard. In these situations the paramedical staff must insert pillows, cushions or other supports underneath the back of the head in an attempt to ensure that the spine is aligned in its natural alignment when viewed horizontally. The placing of pillows, cushions or supports under the back of the head then is a further step requiring handling of the head by the paramedical staff and may interfere with the proportions, angles and other support structure of the head immobilizing device.

SUMMARY OF THE INVENTION

According to the present invention a head immobilizing device to restrain and support the human skull in conjunction with a patient support surface such as a back board or stretcher or the like comprises complimentary left and right support blocks. Each support block includes a base surface and a concave skull supporting surface. The concave skull supporting surface of each block has first and second lobes. The first lobe extends generally vertically upwardly while the second lobe extends generally horizontally and forwardly. There is a L-shaped perimeter edge to the skull supporting surface lying between the first and second lobes. The skull supporting surfaces of the complimentary left and right blocks diverge upwardly and outwardly away from one another so that in use a skull may be supported between the blocks. In order to immobilize the head of the patient the complimentary support blocks are moved from lateral positions one on either side of the head toward the head so that the skull support surface of each block contacts the skull. As the surfaces diverge outwardly and upwardly lateral movement of the blocks toward each other will act as a wedging force to lift the skull vertically upwardly so that the cervical region of the patient may be aligned and the height of the head selected as desired by the paramedical or medical staff. The first generally vertical lobe extends upwardly behind the ear of the patient while the second lobe extends generally horizontally forwardly below the ear of the patient. The L-shaped edge of the skull supporting surface is adapted to accommodate the human ear so that the ear and side of the head of the patient remains available for medical assessment.

The wedging action of the complimentary left and right blocks acting in conjunction with the skull supporting surface eliminates any side to side movement of the head and eliminates any rolling of the head while supporting the head in the vertical direction. If it is desired to prevent lifting of the head by the patient then a strap may be placed across the forehead of the patient with the strap being affixed either to the complimentary left and right blocks or to the patient support surface.

In a particularly inexpensive version which may involve disposable blocks, the complimentary left and right blocks may be manufactured from material such as expanded polystyrene foam. A base surface of each such block may be equipped with an adhesive and advantageously with a small support boss or ribs. The left and right blocks may be slid along the patient support surface along the bosses or ribs until the head is properly captured between the blocks and supported. The blocks may then be pressed vertically downwardly compressing the ribs or bosses so that the adhesive then contacts the patient support surface thereby quickly and easily immobilizing the head. This procedure can be accomplished easily by the paramedic using the two hands to support and position the head both from a side to side and up and down position as desired. Fixation occurs simply by pressing the blocks into the board and contacting the adhesive with the board.

In a more permanent form the device may include a support beam with the complimentary left and right blocks being laterally slidable along the support beam. Advantageously the support beam includes a ratchet or track system and each of the support blocks includes a pawl. With this type of set up the support beam is either in place on the stretcher before the patient or the beam is slid beneath the patient's head and the two blocks are then slide laterally toward the patient's head to similarly position the head as desired. With the left and right support blocks holding the head each pawl is released to hold the blocks in position. Such a device can be manufactured of any relatively permanent equipment that is suitable for re-use and thus may require sterilization. Such equipment can be used in a medical facility and ideally is manufactured from materials that enable use within appropriate diagnostic equipment, such as x-ray equipment, CT scanners and the like.

DETAILED DESCRIPTION OF THE INVENTION

A better and more complete understanding of the invention will be had from reference to the following drawings which illustrate by way of example a preferred embodiment of the invention and in which.

Figure 1:
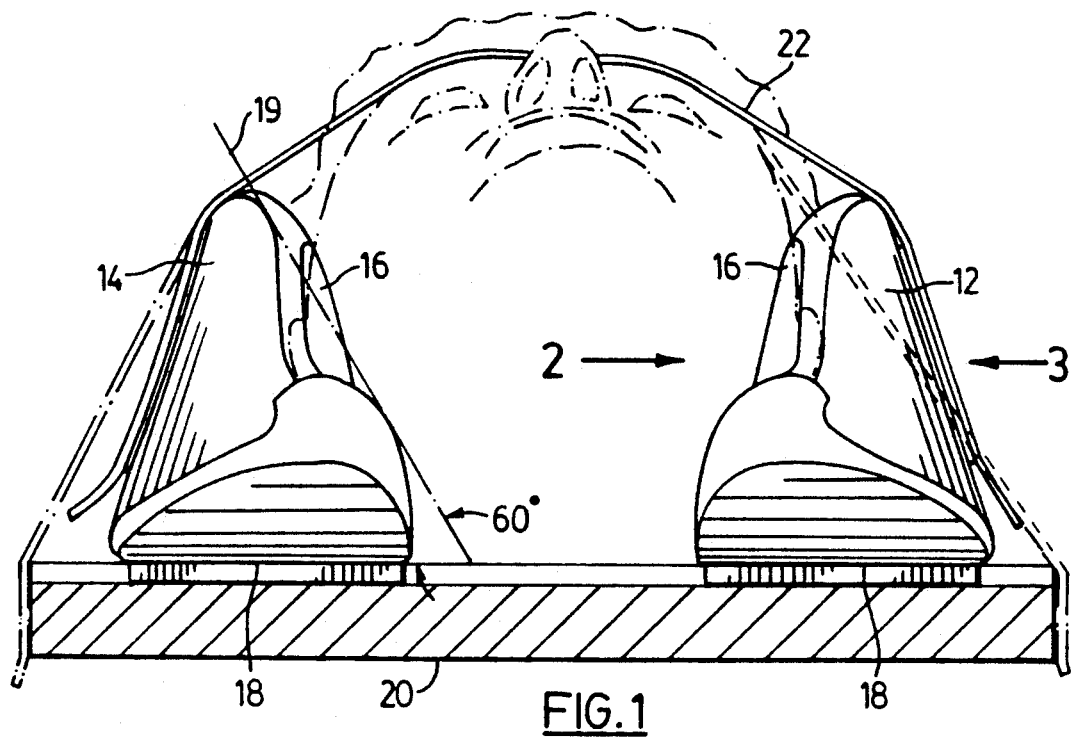
FIG. 1 illustrates a device in accordance with the invention viewed in position on a back board with the patient's head indicated in stippled lines to indicate orientation and location of the support blocks.
Figure 2:
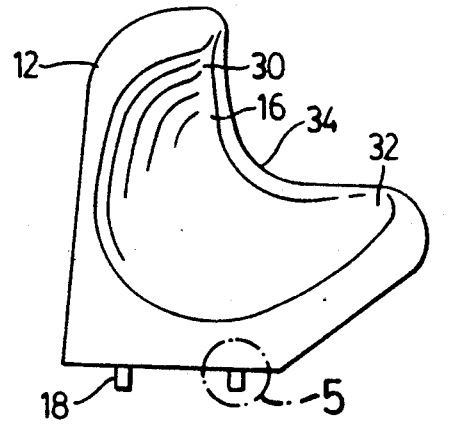
FIG. 2 illustrates one of the blocks of FIG. 1 showing the patient skull supporting surface.

FIG. 1 shows the complimentary left and right blocks 12 and 14. The two blocks are essentially mirror images of each other. As shown in FIG. 1 the two blocks are arranged in use to lie facing each other. Each block comprises a skull supporting surface 16 which is shown in FIGS. 1 and 2 and a base 18. Each of the skull supporting surfaces 16 is a concave surface as shown in FIGS. 1 and 2. The curvature of the concave surface is a compound curvature which is selected to generally conform with the curvature of the average skull. This will be discussed in greater detail below. Although each skull supporting surface 16 is a compound curve the general orientation of the surface is indicated in FIG. 1 by the planar element 19. The angle of the element 19 to the horizontal is approximately 60°. Thus the included angle between the skull supporting surfaces of the left and right blocks is approximately 120°.

It will be appreciated from FIG. 1 that as the complimentary blocks 12 and 14 are moved laterally toward the skull of the patient, the surfaces 16 act as a wedge to lift the skull and position the skull at the desired height. Preferably the general angle of the plane 19 to the horizontal is between 45° and 75° and most preferably is approximately 60°. This gives a good balance of the wedge action to accurately position the height while at the same time supporting the skull regardless of where on the curve the skull contacts the skull supporting surface.

FIG. 2 illustrates the skull supporting surface 16. It will be noted from review of FIG. 2 that the skull supporting surface 16 commences above the base surface 18. As the complimentary support blocks will not be brought into contact with each other there will be some vertical displacement of the point at which the skull contacts the skull supporting surface above the base surface 18. The concave curve to the skull supporting surface 16 is slightly larger than the curve of the average human skull. Thus the area of contact is relatively broad, sufficient to be comfortable and not point contact on the skull while at the same time allowing for different areas of contact on the curve between the skull supporting surface. The precise area where the skull contacts the skull contacting surface will vary depending upon the desired height location of the head above the patient support surface as well as the actual configuration of the curve of the patient's skull. However, the area of contact is significant and thus regardless of where on the surface the skull is contacted the skull cannot move from side to side once the complimentary blocks bear against either side of the skull.

Figure 3:
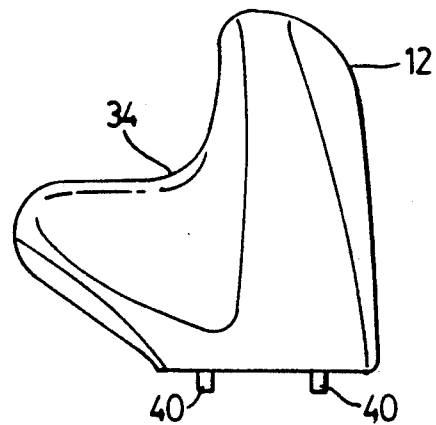
FIG. 3 illustrates the block of FIG. 2 when viewed from the face opposite the face shown in FIG. 2.

Again from review of FIG. 2 it will be observed that the skull supporting surface 16 includes first lobe 30 and second lobe 32. The first lobe 30 extends generally vertically and upwardly. The second lobe 32 extends generally horizontally and forwardly. The skull supporting surface 16 includes a L-shaped perimeter edge portion 34 between the first and second lobes 30 and 32. The L-shaped perimeter edge is adapted to surround the ear of the patient so that the entire ear area is accessible for medical evaluation and treatment. FIG. 3 illustrates the same L-shaped perimeter 34 from the surface of the block which is distal to the skull and further illustrates that the ear of the patient is free for assessment when the blocks are in place immobilizing the skull.

The complimentary blocks as described above serve to fully support the head once the blocks have been positioned and fixed relative to the patient support surface 20. Several different approaches may be taken to locating the blocks with respect to the patient support surface 20. Two particularly advantageous systems however involve firstly disposable blocks which can be used by paramedical staff in ambulances and the like and secondly a much more permanent fixation system which can be used in hospitals for transferring patients to medical assessment equipment such as x-ray equipment, CT scans and the like.

One of the prime considerations in head immobilization equipment to be carried by ambulances and the like is the need to have disposable, lightweight and relatively inexpensive equipment. Particularly in respect of head injuries, it is desirable that once the patient's head has been immobilized on a back support board 20 that the head immobilizing device be left with the patient if at all possible and for as long as possible. Put another way, it is best that the patient be fully assessed without the need to remove the head immobilizing structure. This means in turn that the head immobilizing structured utilized by ambulance attendants and the like should be disposable or intended as a single use device. For these applications it is considered that a particularly advantageous form the device involves the complimentary left and right skull supporting blocks being manufactured from material such as expanded polystyrene foam. Such material is particularly cheap but maintains sufficient rigidity to position and support the head in the manner as discussed above. With disposable blocks of this type it then becomes necessary to provide a simple, cost effective, but strong method of positioning the blocks relative to the patient support surface 20.

Figure 4:
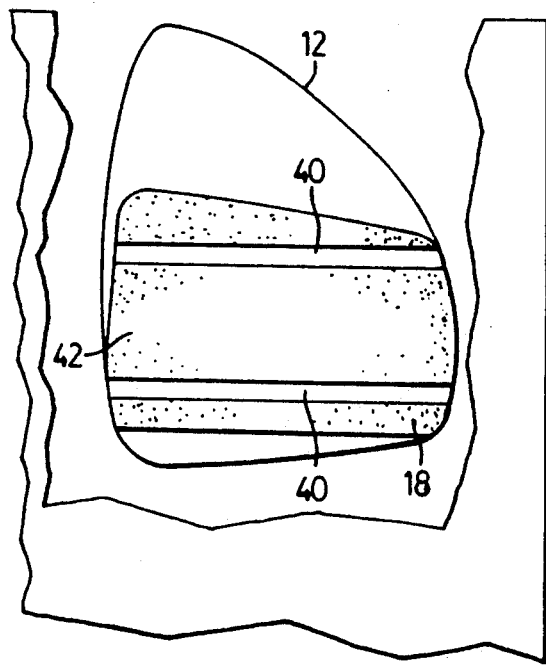
FIG. 4 illustrates the lowermost surface of the block illustrated in FIGS. 2 and 3.
Figure 5:
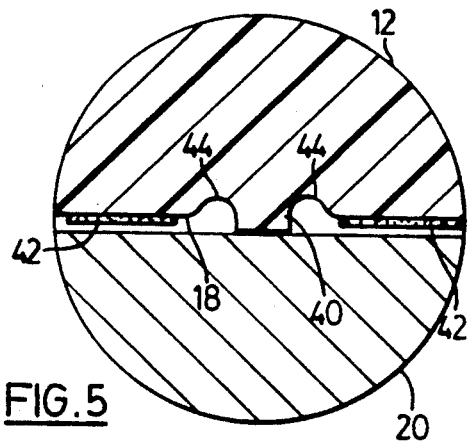
FIG. 5 is an expanded scale view of the encircled portion of FIG. 2, labelled 5.

FIG. 4 illustrates the base surface of a disposable block 12. Extending along the bottom of the base surface 18 there are two ribs 40. The two ribs 40 are also illustrated in FIG. 3. The ribs 40 extend laterally along the base surface of the block 12. Many back boards 20 used for supporting patients include a variety of holes for access, tie downs and lightweight considerations and the like. The ribs 40 advantageously extend laterally the length of the base surface 18 so as to span any holes that may be present in the back board. The ribs are outstanding from the surface 18. If a back board is used which does not have any holes, it may be possible to use circular bosses, buttons or the like outstanding from the surface 18 to provide the spacing function which is discussed hereinafter. With reference to FIG. 4 it will be noted that the base surface 18 of the support block 12 is covered with an adhesive 42. The adhesive 42 may be a pressure sensitive adhesive and is used to affix the support block to the patient support surface 20. A cross-sectional view on an enlarged scale of one of the ribs 40 is illustrated in FIG. 5. Most preferably the rib 40 is accompanied on either side by a relieved channel 44 which extends below the surface 18.

The purpose of the rib 40 is to space the adhesive 42 from the surface of the patient support surface 20 until it is desired to affix the support block to the patient support surface. Thus, the support blocks are supported on the patient support surface by the ribs 40 during the initial positioning step. When the support blocks have been positioned to appropriately support and immobilize the skull then vertical downward pressure is placed on the support blocks 12 and 14. The downward pressure is sufficient to compress the ribs 40. In order to assist in the compression of the rib 40, the channels 44 provide a void area into which the compressed rib 40 may flow under compression. The compressing of the rib 40 thus brings the pressure sensitive adhesive 42 into contact with the surface of the patient supporting device 20 and the support block is then fixed to the patient supporting device.

In many cases it may be desirable that the patient does not attempt to lift his or her head. In order to guard against this type of motion a strap 22 may be placed over the forehead of the patient and affixed to the patient supporting surface 20. The strap 22 may be affixed directly to the patient supporting surface 20 such as by adhesive, hook and loop fasteners or the like or the strap 22 may be affixed to the patient supporting surface 20 through the intermediary of the left and right support blocks. It is considered that it is most preferable to affix the strap directly to the patient support surface 20.

Figure 6:
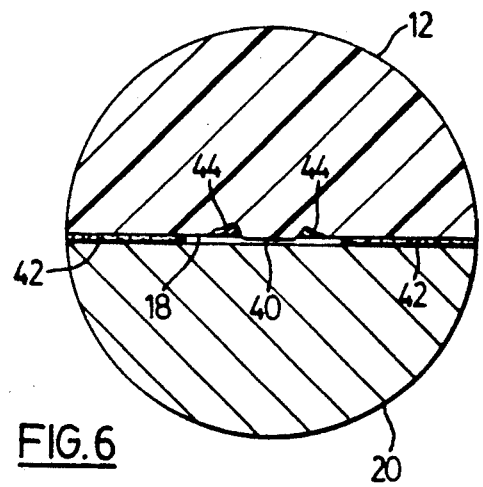
FIG. 6 is a view of the block and board of FIG. 5 with the block having been adhered to the patient support board.
Figure 8:
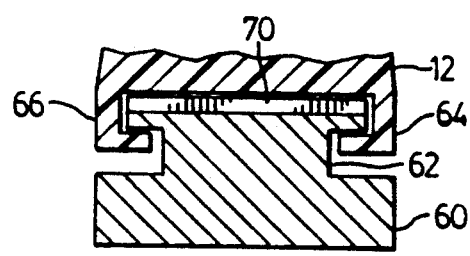
FIG. 8 is a cross-section through the support track and the bottom portion of the block of FIG. 7.
Figure 7:
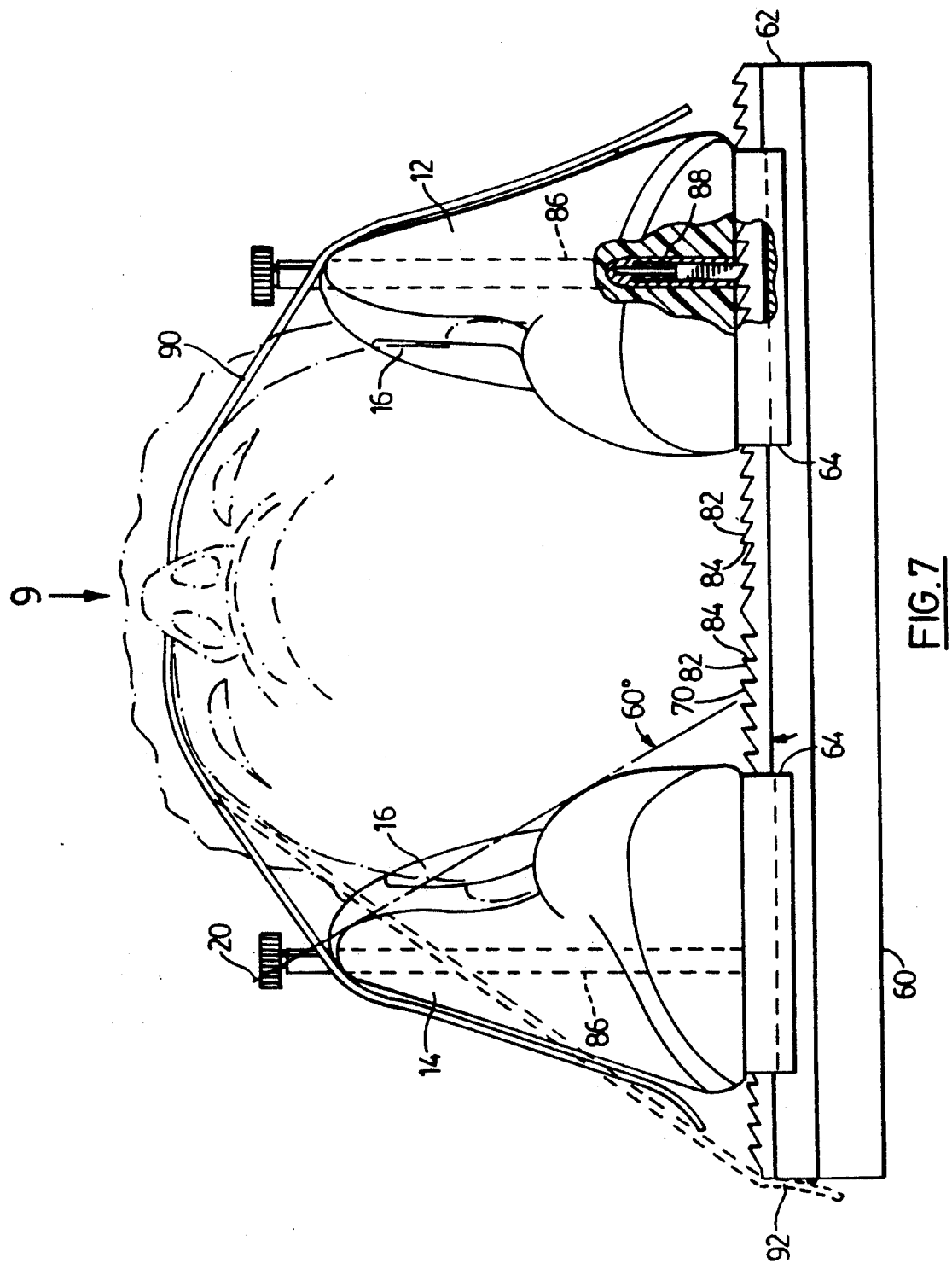
FIG. 7 is a view of an alternate embodiment of the invention similar to FIG. 1.

A reusable form of the device is illustrated in FIGS. 6, 7 and 8. In this embodiment the complimentary left and right skull supporting blocks 12 and 14 are essentially similar to those as discussed above. However, the material from which the blocks are made may differ considerably in view of the fact that the device is to be reused. Preferably the material is material which can be sterilized and which does not adversely effect various medical assessment tools such as x-ray equipment, CT scanners and the like. Ideally the entire device may be made from polyethylene which meets all of these requirements.

The device illustrated in FIG. 6 comprises complimentary skull support blocks 12 and 14 and a support beam 60.

Figure 9:
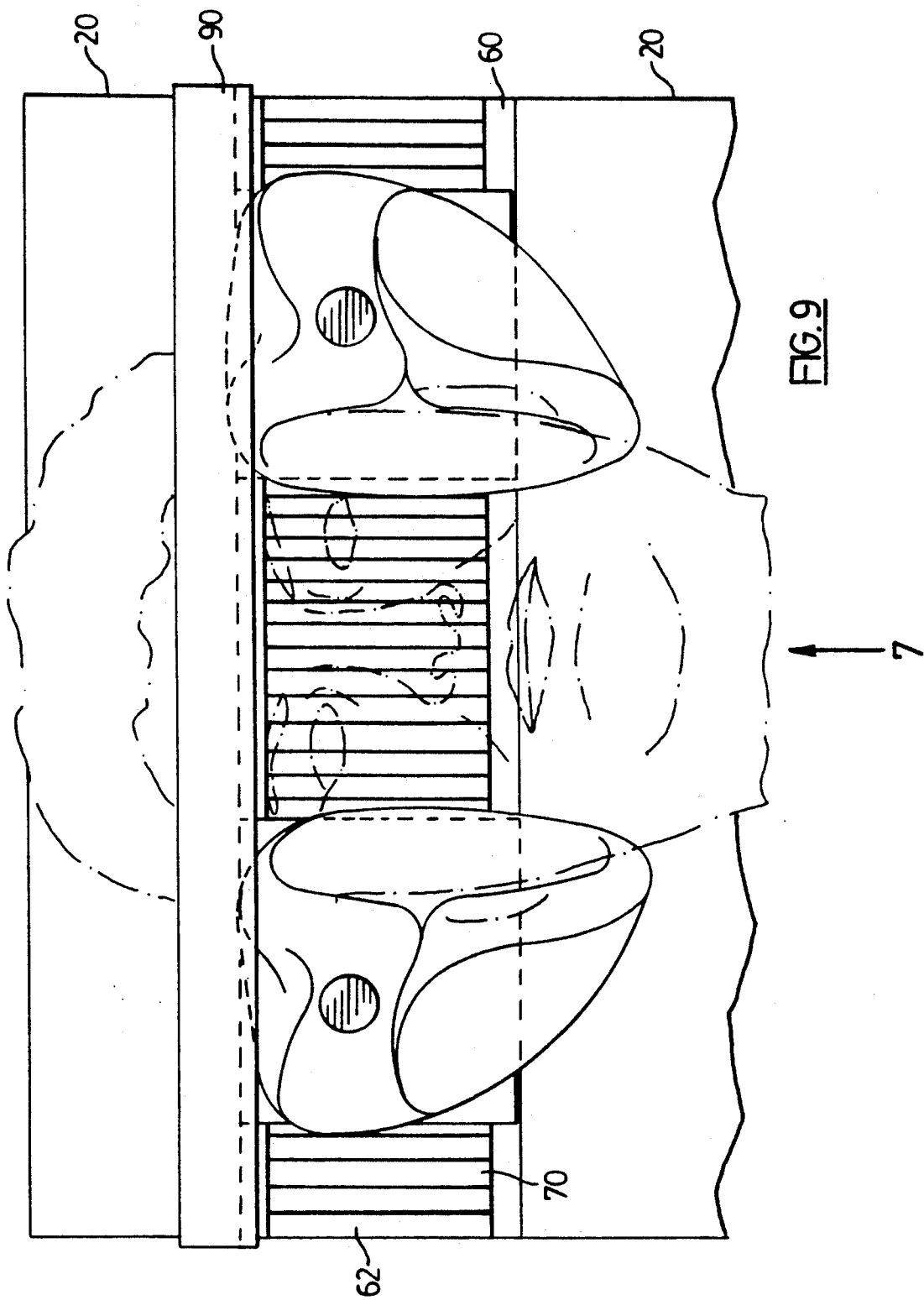
FIG. 9 is a top view of the embodiment of FIG. 7 illustrating the patient's head in stippled lines.

The interrelation between the support beam 60 and the block 12 is more clearly shown in FIGS. 7, 8 and 9.

The support beam 60 comprises a track 62. The track 62 is a T-shaped projection in the upper surface of the support beam 60. With this configuration the base surface of the skull support block 12 comprises downwardly and inwardly projecting skirts 64 and 66. The interrelation of the track 62 and the skirts 64 and 66 prevents any vertical movement between the support beam 60 and the support block 12. In order to load the support block on the support beam 60, the support block must be slid from one end onto the support beam 60.

The upper surface of the track 62 advantageously comprises a plurality of serrations or teeth 70. These are shown in larger scale in FIG. 7. The teeth 80 are provided with a sloped surface 82 and a substantially vertical surface 84. The sloped surface 82 slopes upwardly and inwardly toward the middle of the support beam 60. That is to say, the sloped surface extends inwardly from each end. The teeth 80 inter-react with a pawl 86 carried by the support blocks 12 and 14. The pawl 86 may be in the form of a pin or in the form of a substantially rectangular tongue. Advantageously the pawl 86 projects upwardly through the outer surface of the blocks 12 and 14 and is spring loaded by means of a spring 88 biasing the pawl downwardly. With this structure the support blocks 12 and 14 may be loaded onto the support beam 60 by aligning the skirt 64, 66 with the track 62. As the blocks are slid inwardly towards the centre of the track, the pawl will ride up the sloped surfaces 82 and thus the support blocks can be slid freely and easily with one hand toward each other, toward the patient's skull. When it is desired to remove the skull supporting blocks 12 and 14 from adjacent the patient's skull, then the pawl 86 is lifted by inserting a finger and raising the pawl against the spring 88. The support blocks can then be slid outwardly as the pawl no longer engages the vertical surface 84 against which it was locked for outward motion.

As shown in FIGS. 7 and 9 a strap 90 may be used to further secure a patient's head against vertical motion. The strap 90 may be joined to the skull support blocks 12 and 14 by means of buckles or by hook and loop fasteners or the like. In this case the support blocks 12 and 14 are securely vertically affixed to the support beam 60 and thus the strap 90 advantageously extends only between the support blocks 12 and 14 and does not need to extend down to the support beam 60 or the patient support surface 20 on which the patient is lying.

The support beam 60 may be fastened to the patient support surface 20 by any convenient means. If the support beam is to be used with a typical back board then the support beam may include a pivoted latch 92 of either end which can grasp the edge of the back board. Where the beam is used with a stretcher, straps with buckles or other closures may be utilized.

The colours red and green are widely recognized and internationally accepted as indications of left and right sides. The colours are used in connection with ships and aircraft to identify such vessels to other vessels and as navigation aids. In the first embodiment of the device described above it was pointed out that the devices are advantageously maintained by ambulance attendants and the like for quick ready use. Because the devices are in the form of left and right complimentary blocks it is likely that ambulance attendants will wish to carry more than one set of such blocks. In order to assist in the quick and ready utilization there is an advantage in coding the left and right blocks so that they can be instantly recognized by the ambulance attendant. For this reason it is suggested that some or at least a portion of the block which is to contact the left side of the patient's skull be coloured red while a similar portion of the right side block should be coloured green. The colour indication may be in the form of complete colouration of the whole surface, a patch of colour, colour stripes or the like. In any case this will help to assist the ambulance attendant or the like, using the blocks to ensure that he has a pair of blocks and which block should be grasped by which hand in order to immobilize the patient's skull. The colour coding is less important in the more permanent version discussed in association with FIGS. 7, 8 and 9. However, even in these cases it may be advantageous to mark the left and right extremities of the device. This may include marking of the blocks themselves or by markings or the end of the support track so that the support track may be positioned correctly. While this should be obvious to the operator within a medical facility, colour marking of this type may be advantageous to ensure that the blocks are brought into contact with the skull with the orientation as illustrated in the figures herein.

While generally speaking a strap extending across the forehead region may be used as shown in FIGS. 1 and 9, a strap cannot be placed across the forehead where there is reason to suspect there has been damage to the skull in this area. Accordingly, when there is suspicion of a depressed fracture of the skull in the forehead region a strap should not be applied to that area of potential injury. In this case an immobilizing strap may be attached to the patient's head by extending around an obviously uninjured area. This may mean using these straps between the patient's jaw and the left and right blocks or the nose or cheek bones or the like, all as may be available without increasing damage which the patient may have already suffered. In such circumstances, the left and right blocks as disclosed herein provide particularly suitable anchor points for immobilization when the patient's forehead does not appear to be an acceptable choice for strap location.

From review of this description it will observed that a simple, effective device has been disclosed which serves to both locate the patient's skull with respect to side to side motion while at the same time providing a means to vertically position the skull in the most advantageous position. Quick and easy adjustment of the skull support blocks may be achieved. While the device is in place supporting and immobilizing the skull from any further movement, the head and ear remains available for further medical assessment and the patient can be placed in a standard cervical collar. It will be appreciated that many variations and changes may be made to the structure as disclosed herein without departing from the scope of the invention as defined in the appended claims.

I claim:

1. A head support to be used to restrain and support the human skull and cervical spine in conjunction with a patient support surface comprising complimentary left and right support blocks each support block comprising a base surface and a concave skull support surface, said support surface having first and second lobes, said first lobe extending generally vertically, upward in a plane generally parallel to the spine and said second lobe extending generally horizontally and forwardly in a plane generally parallel to the spine, said concave skull support surface having a U-shaped perimeter edge between said first and second lobes, said first and second lobes and said U-shaped perimeter edge shaped and adapted to support said skull around the ear, so that the ear is available for diagnostic checking when the skull is supported by said support surface, the skull support surfaces of said complimentary left and right blocks diverging upwardly and outwardly away from one another so that in use a skull may be supported between said blocks and the vertical position of the skull relative to the patient support surface may be determined by the relative location of the blocks.

2. The device of claim 1 wherein said support blocks comprise a skull support surface which is inclined to the horizontal at an angle of from about 45° to about 75°.

3. The device of claim 1 wherein said support blocks comprise a skull support surface which is inclined to the horizontal at an angle of from about 60°.

4. The device of claim 1 wherein each support block includes fixation means for locating said block with respect to a patient support surface.

5. The device of claim 1 wherein said fixation means comprises a pressure sensitive adhesive on said base surface.

6. The device of claim 5 wherein each said block comprises at least one deformable rib projecting from said base surface.

7. The device of claim 6 wherein said base surface of said block includes a relieved channel adjacent said rib to receive said rib on deformation.

8. The device of claim 7 wherein said support blocks are made from expanded foam.

9. The device of claim 7 wherein said left block is marked with the colour red and said right block is marked with the colour green.

10. The device of claim 6 wherein each said block comprises two deformable ribs projecting from said base surface and said base surface includes a relieved channel adjacent each said rib to receive said rib on deformation.

11. The device of claim 1 wherein said head support includes a support beam, said support beam including fixation means for co-operation with said fixation means of said left and right blocks for attaching said support blocks to said support beam.

12. The device of claim 11 wherein said support beam includes a track and said support blocks are adapted to slide laterally along said track.

13. The device of claim 12 wherein said support beam incudes ratchet means co-operating with releasable pawl means on each of said blocks so that said blocks may be slid freely toward one another along said track and said pawl and said ratchet prevent outward movement when said pawl and said ratchet are engaged.

14. The device of claim 13 wherein said strap extends to said support beam.

15. The device of claim 14 wherein said support surface is a back board.

16. The device of claim 14 wherein the support surface is a stretcher.

17. The device of claim 12 further including a strap adapted to engage the forehead of the patient and extend between said left and right blocks.

18. The device of claim 17 further including means to affix said support beam to the patient support surface.

19. The device of claim 11 wherein said device comprises colour marking to indicate left and right sides of the device, said left side bearing a marking in the colour red and said right side bearing a marking in the colour green.

* * * * *